United States Patent [19]

Roscher et al.

[11] 4,380,663

[45] Apr. 19, 1983

[54] PROCESS FOR THE PREPARATION OF PRACTICALLY FORMIC ACID-FREE ACETIC ACID

[75] Inventors: Günter Roscher, Kelkheim; Helmut Schaum, Bad Soden am Taunus; Heinz Schmitz, Frankfurt am Main, all of Fed. Rep. of Germany

[73] Assignee: Hoechst Aktiengesellschaft, Frankfurt am Main, Fed. Rep. of Germany

[21] Appl. No.: 844,048

[22] Filed: Oct. 20, 1977

Related U.S. Application Data

[63] Continuation of Ser. No. 670,412, Mar. 25, 1976, abandoned.

[30] Foreign Application Priority Data

Mar. 27, 1975 [DE] Fed. Rep. of Germany ....... 2513678
Dec. 18, 1975 [DE] Fed. Rep. of Germany ....... 2557004

[51] Int. Cl.$^3$ .................... C07C 51/235; C07C 53/08
[52] U.S. Cl. .................................. 562/536; 202/158; 423/437; 560/238; 585/733
[58] Field of Search ...................... 260/530R; 562/536

[56] References Cited

U.S. PATENT DOCUMENTS

| | | | |
|---|---|---|---|
| 1,951,789 | 3/1934 | Mueller-Cunradi et al. | ... 260/530 R |
| 2,170,002 | 8/1939 | Benson | ............................. 260/530 R |
| 2,355,140 | 8/1944 | Bludworth | ...................... 260/530 N |

*Primary Examiner*—Vivian Garner
*Attorney, Agent, or Firm*—Curtis, Morris & Safford

[57] ABSTRACT

A process is provided for the preparation of practically formic acid-free acetic acid by oxidation of acetaldehyde in the liquid phase with oxygen or oxygen-containing gases in the presence of mixtures of cobalt, nickel and manganese salts as catalysts.

7 Claims, 1 Drawing Figure

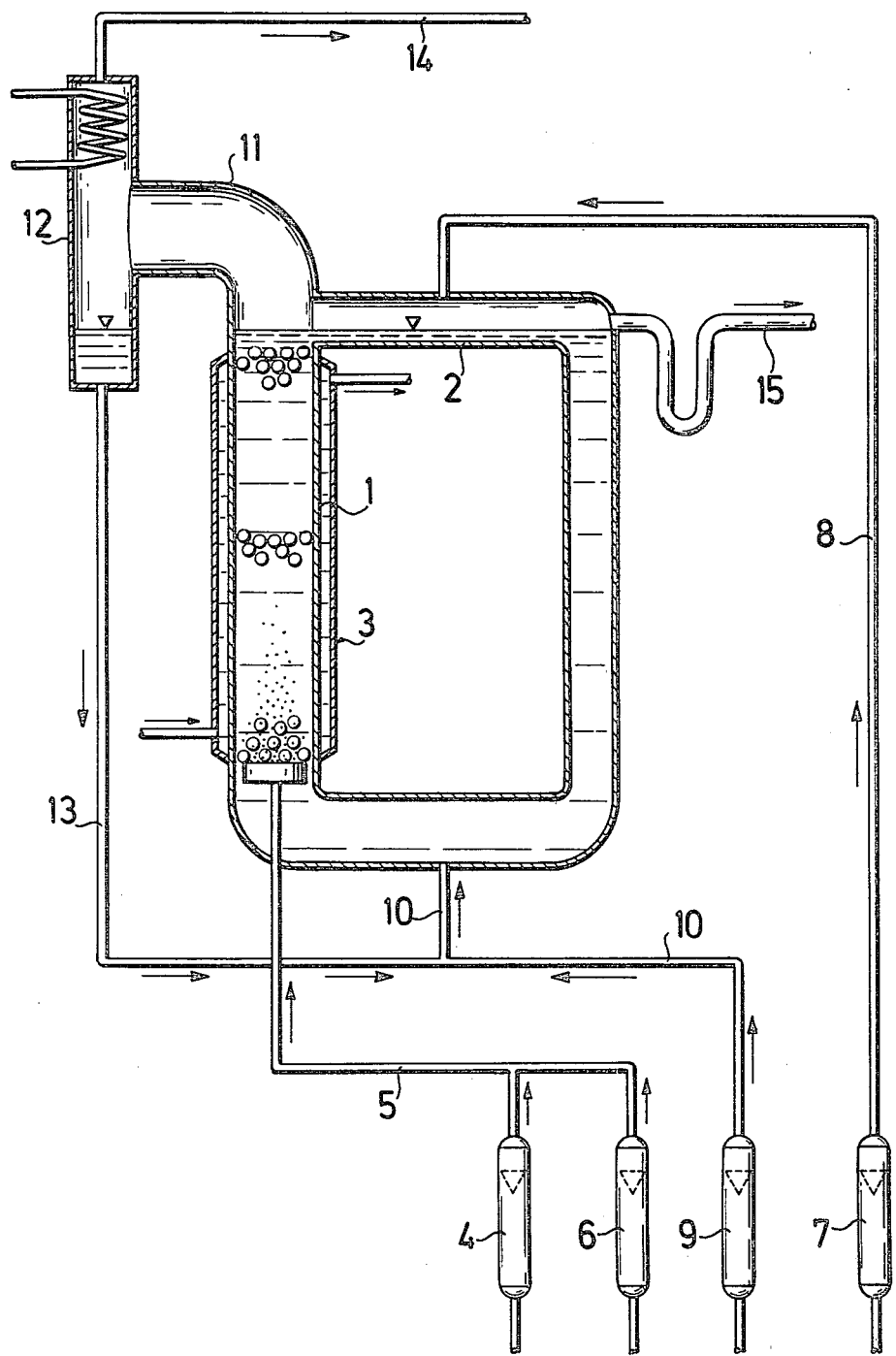

PROCESS FOR THE PREPARATION OF PRACTICALLY FORMIC ACID-FREE ACETIC ACID

This is a continuation, of application Ser. No. 670,412, filed Mar. 25, 1976, now abandoned.

The present invention relates to a process for the preparation of practically formic acid-free acetic acid.

Acetic acid is manufactured on an industrial scale according to various methods. Apart from oxidation of hydrocarbons, oxidation of ethanol and reaction of carbon oxide with methanol under pressure, oxidation of acetaldehyde with oxygen or air in the presence of catalysts is one of the processes most frequently applied. As catalysts in this process there are generally used salts of manganese, cobalt, copper, vanadium, uranium, nickel, iron or cerium. In addition to carbon oxide and methane, a number of liquid by-products are formed in this process, for example water, acetone, methyl acetate, methanol, methyl formate and formic acid. When the crude acetic acid product is worked up by distillation to form pure acetic acid, elimination of the last approximately 0.5% of the formic acid in the crude acetic acid is very difficult.

Because of the required quality of pure acetic acid, however, the formic acid amount has to be eliminated nearly completely, leaving an insignificant residue only. A zone of high formic acid concentration becomes established in the distillation column which then, must be operated with extensive refluxing in order to eliminate said formic acid. Because of the corrosive properties of formic acid, distillation columns must be made from special materials, for example titanium, instead of the cheaper stainless steel. Furthermore, the elimination of formic acid by distillation always involves losses of acetic acid, since the separated formic acid still contains acetic acid.

A number of methods for elimination or decomposition of formic acid contained in acetic acid are already known, for example distillation of the formic acid with the use of special azeotrope-forming agents, or catalytic decomposition of the formic acid in the presence of catalysts in the gaseous or liquid phase, or elimination by reaction with acetic acid anhydride. The hitherto known methods of elimination or separation of formic acid, however, require additional apparatus and auxiliaries. Processes which prevent the formation of formic acid in the acetaldehyde oxidation step have not been proposed heretofore.

The present invention now provides a process for the preparation of practically formic acid-free acetic acid by oxidation of acetaldehyde in the liquid phase with oxygen or oxygen containing gases in the presence of catalysts, wherein the catalyst system contains mixtures of cobalt, nickel and manganese compounds.

The cobalt, nickel and manganese compounds are always simultaneously present in the process of the invention. Suitable compounds are halides, sulfates, nitrates, or carboxylates, preferably acetates. These salts are generally introduced into the reaction in aqueous or acetic acid solutions.

The weight ratio of the individual components of the catalyst mixture is not critical. Generally, it is 1:1:1, but each of the individual components may be present in an amount up to five times the sum of the amounts of both the other components. The catalyst concentration in the reaction solution is not critical either; generally, it is from 0.05 to 0.5 weight % for each of the three components, relative to the aldehyde used. Lower or higher concentrations, however, may also be applied.

The process of the invention is generally carried out under a pressure ranging from normal to 5 bars overpressure, preferably from normal to 3 bars overpressure.

The reaction temperature is generally in a range of from 40° to 120° C., preferably from 50° to 80° C.

By means of the process of the invention, the formic acid concentration in the crude acetic acid is decreased to 100 ppm. Thus, the present invention represents a considerable technical advance. The fact that formic acid is contained only in traces from the beginning in the crude acetic acid obtained allows the use of normal stainless steel as construction material for the distillation columns where the crude acetic acid is worked up to industrial-grade purity, instead of special materials of higher cost. Moreover, the amounts of acetic acid lost by discharge together with the very small residual amounts of formic acid decrease considerably. Furthermore, the separation operations for obtaining pure acetic acid may be carried out much more economically now, since the other by-products, with considerably less refluxing, are eliminated more easily in the distillation column than formic acid.

An advantage of using the catalysts of this invention resides in the fact that by-products such as methanol, methyl acetate, $CO_2$, $CH_4$ and $H_2O$ are not formed in increased amounts, and that the acetic acid yield, relative to the acetaldehyde charged, is not decreased. Several of the catalysts previously known, especially those containing mixtures of cobalt and nickel salts, keep the formation of formic acid low but increase that of the other by-products, and thus cannot be used on an industrial scale because of the cost for the corresponding high acetaldehyde consumption. It is surprising that the catalyst combination of this invention meets all the requirements, while the known individual components, alone or in combination may reduce the formation of formic acid but increase that of other by-products.

A further advantage of the process of the invention, as compared to those large-scale processes employing mostly manganese acetate as catalyst, resides in the possibility of reusing the catalyst-containing residue for the reaction after having distilled off the acetic acid obtained.

The consumption of catalyst is therefore limited to the amount required for a single reactor charge and the normal leakage losses.

The activity of the catalyst combination in accordance with the present invention is not disturbed by the presence of other salts, for example of iron, chromium, molybdenum, titanium, etc. When the catalyst is recirculated in continuous operation, these components may gradually concentrate in the catalyst solution, because they are formed by a slight corrosion of the apparatus materials due to the acetic acid.

This invention will be better understood by reference to the accompanying drawing which represents an especially recommended operation mode of the process.

The reactor (1) consists of a tube with a jacket having an inner diameter of 50 mm and a height of 50 cm, measured up to the coupled cross tube (2) for the circulation of the liquid. The reactor temperature is adjusted by thermostat-heated water circulating in the jacket (3). In order to ensure a better oxygen distribution, the reactor (1) provided with a jacket is charged with Raschig rings (6×6 mm) of stainless steel mesh. Oxygen is fed to the reactor (1) via flowmeter (4) and duct (5). For safety reasons, the oxygen is diluted with a small amount of nitrogen, fed to the oxygen duct (5) via flowmeter (6). Furthermore, in order to reduce the oxygen concentration in the gas zone over the reactor liquid and to make this zone inert, additional nitrogen is fed to reactor (1) via flowmeter (7) and duct (8). The acetaldehyde containing the catalyst dissolved in acetic acid is fed to reactor (1) via flowmeter (9) and duct (10). The gas mixture leaving the reactor (1) via tube (11) and containing nitrogen, non-consumed oxygen, $CO_2$ and methane, unreacted acetaldehyde and reactor liquid vaporized in an amount depending on the reactor temperature and the partial pressure is cooled to about 25° C. in the condenser (12) provided with a cooling lake. The condensed amounts are recycled to the reactor via duct (13), and the remaining gas is let off via duct (14). The crude acetic acid is taken off via duct (15).

A special embodiment of the process of the invention is the following. The partial streams, formed in the distillation work-up of the crude acetic acid to pure acetic acid and containing a very small amount of formic acid, are recycled into the oxidation zone of the acetaldehyde. In detail, operation is as follows: the small partial stream, formed in the distillation work-up of crude acetic acid to pure formic acid-free acetic acid and containing the main part of the very small amount of formic acid formed is not separated in further distillation steps into formic and acetic acid. Instead this partial stream is recycled to the reactor where the oxidation of acetaldehyde to acetic is carried out. Surprisingly, the formic acid recycled is destroyed. This operation mode yields formic acid-free acetic acid without any loss of acetic acid, simultaneously avoiding expensive further work-up.

The following examples illustrate the invention. N in Nl stands for "normal", that is, at 0° C. and 760 mm Hg.

COMPARATIVE EXAMPLE 1

The reactor was charged with the following amounts per hour:

(a) 312 g of a mixture of 80 weight % of acetaldehyde and 20 weight % of acetic acid, which mixture contained 0.15 weight % of manganese acetate, fed in via flowmeter 9 and duct 10, (b) 120 Nl of oxygen fed in via flowmeter 4 and duct 5

(c) 20 Nl of nitrogen fed in via flowmeter 6 and duct 5

(d) 80 Nl of nitrogen fed in via flowmeter 7 and duct 8.

The reaction temperature was adjusted to 60° C. 360 g/h of crude acetic acid composed as follows were taken off via duct 15:

95.9 weight % of acetic acid
2.1 weight % of water
1.2 weight % of acetaldehyde
0.4 weight % of formic acid
0.4 weight % of methyl acetate and other products.

168 Nl of gas composed as follows were discharged per hour via duct 14:

59% by vol. of nitrogen
29.8% by vol. of oxygen
7.1% by vol. of carbon dioxide
2.7% by vol. of methane
1.3% by vol. of acetaldehyde.

An acetaldehyde conversion rate of 96% was calculated on the amounts of gas and crude acetic acid. The amount of formic acid formed was 0.5 weight % of the acetic acid obtained. 6.7% of the converted acetaldehyde reacted to form $CO_2$ and methane.

COMPARATIVE EXAMPLE 2

Test apparatus, test conditions and quantities used were the same as in Comparative Example 1. However, instead of manganese acetate, 0.15 weight % of cobalt acetate was dissolved in the starting mixture of acetic acid/acetaldehyde.

351 g/h of crude acetic acid composed as follows were obtained:

92.0 weight % of acetic acid
5.0 weight % of water
2.0 weight % of acetaldehyde
0.5 weight % of formic acid
0.5 weight % of methyl acetate and other products.

172 Nl/h of gas composed as follows were discharged via duct 14:

58% by vol. of $N_2$
10.4% by vol. of $CO_2$
3.1% by vol. of $CH_4$
24.5% by vol. of $O_2$
4.0% by vol. of acetaldehyde.

The acetaldehyde conversion rate was 91%; 10% of the converted acetaldehyde reacted to form carbon dioxide and methane. The amount of formic acid formed was 0.7 weight % of the acetic acid obtained.

COMPARATIVE EXAMPLE 3

Test apparatus, test conditions and quantities used were the same as in Example 1. However, instead of manganese acetate, the acetic acid/acetaldehyde starting mixture contained 0.15 weight % of nickel acetate as catalyst.

300 g/h of crude acetic acid composed as follows were obtained:

84.4 weight % of acetic acid
8.3 weight % of water
5.0 weight % of acetaldehyde
0.12 weight % of formic acid
0.6 weight % of methyl acetate and other products.

201 Nl/h of gas composed as follows were discharged via duct 14:

49.5% by vol. of $N_2$
13.5% by vol. of $CO_2$
3.5% by vol. of $CH_2$
19.4% by vol. of $O_2$
13.2% by vol. of acetaldehyde.

The acetaldehyde conversion rate was 73%. The amount of formic acid formed was 0.2 weight % of the acetic acid obtained. 20% of the converted aldehyde reacted to form carbon dioxide/methane. As compared to Comparative Example 1, the amount of formic acid was somewhat reduced, but the amount of $CO_2$ and methane is considerably increased.

COMPARATIVE EXAMPLE 4

Test apparatus, test conditions and quantities used were as in Comparative Example 1. The acetic acid-/acetaldehyde starting mixture contained 0.15 weight % of manganese acetate and 0.15 weight % of cobalt acetate as catalyst.

367 g/h of crude acetic acid composed as follows were obtained:

92.7 weight % of acetic acid
4.8 weight % of water
1.9 weight % of acetaldehyde
0.25 weight % of formic acid
0.35 weight % of methyl acetate and other products.
169 Nl/h of gas composed as follows were discharged via duct 14:
  59.2% by vol. of $N_2$
  10.6% by vol. of $CO_2$
  3.0% by vol. of $CH_4$
  22.5% by vol. of $O_2$
  4.7% by vol. of acetaldehyde.

The acetaldehyde conversion rate is 92%. The amount of formic acid formed is 0.3 weight % of the acetic acid obtained. 10% of the converted acetaldehyde reacted to form $CO_2$ and methane.

COMPARATIVE EXAMPLE 5

Test apparatus, test conditions and quantities used were as in Comparative Example 1. The acetic acid/acetaldehyde starting mixture contained 0.15 weight % of manganese acetate and 0.15 weight % of nickel acetate as catalyst.

368 g/h of crude acetic acid composed as follows were obtained:
  94.35 weight % of acetic acid
  3.8 weight % of water
  1.3 weight % of acetaldehyde
  0.25 weight % of formic acid
  0.3 weight % of methyl acetate and other products.
167 Nl/h of gas composed as follows are discharged via duct 14:
  59.7% by vol. of $N_2$
  9.3% by vol. of $CO_2$
  3.0% by vol. of $CH_4$
  25.3% by vol. of $O_2$
  2.7% by vol. of acetaldehyde.

The acetaldehyde conversion rate is 95.4%, the formic acid amount formed is 0.3 weight % of the acetic acid obtained, and 9% of the converted acetaldehyde reacted to form $CO_2$ and methane.

COMPARATIVE EXAMPLE 6

Test apparatus, test conditions and quantities are as in Comparative Example 1. The acetic acid/acetaldehyde starting mixture contained 0.15 weight % of nickel acetate and 0.15 weight % of cobalt acetate.

362 g/h of crude acetic acid composed as follows are obtained:
  92.4 weight % of acetic acid
  6.1 weight % of water
  1.1 weight % of acetaldehyde
  0.06 weight % of formic acid
  0.34 weight % methyl acetate and other products.
171 Nl/h of gas composed as follows are discharged via duct 14:
  58.7% by vol. of $N_2$
  14.5% by vol. of $CO_2$
  5.2% by vol. of $CH_4$
  17.5% by vol. of $O_2$
  4.1% by vol. of acetaldehyde.

The acetaldehyde conversion rate was 93.3%. 14.3% of the converted acetaldehyde reacted to form carbon dioxide and methane, and the formic acid amount formed is 0.08 weight % of the acetic acid obtained.

EXAMPLE 1

Test apparatus, test conditions and quantities used were as in Comparative Example 1. The acetic acid/acetaldehyde starting mixture contained 0.05 weight % of manganese acetate, 0.05 weight % of cobalt acetate and 0.05 weight % of nickel acetate.

370 g/h of crude acetic acid composed as follows were obtained:
  96.6 weight % of acetic acid
  1.7 weight % of water
  1.1 weight % of acetaldehyde
  0.02 weight % of formic acid
  0.3 weight % of methyl acetate and other products
179 Nl/h of gas composed as follows were discharged via duct 14:
  56% by vol. of $N_2$
  5.7% by vol. of $CO_2$
  1.7% by vol. of $CH_4$
  32.4% by vol. of $O_2$
  4.2% by vol. of acetaldehyde The acetaldehyde conversion rate is 92%. The formic acid amount formed was 0.025 weight % of the acetic acid obtained. 5.5% of the converted acetaldehyde reacted to form carbon dioxide and methane.

EXAMPLE 2

Test apparatus, test conditions and quantities used were as in Comparative Example 1. The acetic acid/acetaldehyde starting mixture however contained 0.15 weight % of manganese acetate, 0.15 weight % of nickel acetate and 0.15 weight % of cobalt acetate.

400 g/h of crude acetic acid composed as follows were obtained:
  97.2 weight % of acetic acid
  1.4 weight % of water
  1.0 weight % of acetaldehyde
  0.01 weight % of formic acid
  0.3 weight % of methyl acetate/other products.
172 Nl/h of off-gas composed as follows were discharged via duct 14:
  58.3% by vol. of $N_2$
  36.7% by vol. of $O_2$
  2.4% by vol. of $CO_2$
  0.8% by vol. of $CH_4$
  0.6% by vol. of acetaldehyde.

An acetaldehyde conversion rate of 97.5% was calculated on the amounts of gas and crude acetic acid obtained. 4.5% of the converted aldehyde reacted to form $CO_2$ and methane.

EXAMPLE 3

Operations were carried out under the test conditions indicated in Comparative Example 1, as were the quantities of gaseous substances fed to the reactor indicated there. However, the amount of liquid acetaldehyde/acetic acid mixture fed in per hour was only 265 g, and this mixture contained 0.15 weight % of manganese acetate, 0.03 weight % of cobalt acetate and 0.03 weight % of nickel acetate.

323 g of crude acetic acid composed as follows were obtained per hour:
  97.5 weight % of acetic acid
  1.8 weight % of water
  0.1 weight % of acetaldehyde
  0.05 weight % of formic acid 0.35 weight % of methyl acetate and other low-boiling substances. The crude acetic acid was continuously forwarded to a vaporizing alembic, where the low-boiling substances and the greater part of the acetic acid were distilled off. Vaporization was continued until the evaporator bottom contained about 5 weight % of manganese acetate and 1 weight % each of nickel acetate and cobalt acetate. From the evaporator bottom, 110 g/h of bottom product were taken off and recycled to the reactor (without cooling in order to avoid manganese acetate precipitation). When, by means of the catalyst cycle, a manganese acetate concentration of 1.5 weight % was established in the reactor, the addition of manganese nickel and cobalt to the acetaldehyde/acetic acid starting mixture was stopped, that is, operations were carried out without fresh catalyst and with circulation of the catalyst previously fed in only. The distillate of the vaporizer alembic, which corresponded to the crude acetic acid (without catalyst) with respect to composition and quantity, was continuously worked up in two further distillation columns. The first column was a glass bubble-cap column having a diameter of 40 mm and provided with a circulating evaporator and automatic reflux distributor. The column had 50 bubble-plates, the inlet being on the 20th plate. At a reflux rate of 10, about 25 g of distillate per hour were obtained, which were composed as follows:

70 weight % of acetic acid
23.4 weight % of water
0.7 weight % of formic acid
1.3 weight % of acetaldehyde
4.6 weight % of methyl acetate and other substances.

The bottom products discharged are pure, practically formic acid-free acetic acid.

The above distillate was further worked-up continuously, in another bubble-cap column having 50 plates. The inlet being on the 25th plate. At a reflux rate of 15, acetaldehyde, methyl acetate and water were taken off as top product. As bottom product, there were obtained 18 g/h of a mixture composed as follows:

97.1 weight % of acetic acid
0.9 weight % of formic acid
2.0 weight % of water

This mixture was recycled to the reactor. After the equilibrium of the complete system has established, there was no increase of formic acid concentration in the crude acetic acid. The concentration was from 0.03 to 0.05 weight %. The recycled formic acid was destroyed in the reactor.

What is claimed is:

1. In a process for the preparation of acetic acid substantially free of formic acid by oxidation of acetaldehyde with oxygen in the liquid phase in the presence of a catalyst at a temperature of from 40° C. to 120° C., the improvement which comprises oxidizing liquid acetaldehyde in the presence of a catalytic mixture of cobalt, nickel, and manganese compounds, one of said compounds being present in an amount up to five times the sum of the amounts of the other compounds.

2. The process as defined in claim 1, wherein said compounds are selected from the group consisting of halides, sulfates, nitrates and carboxylates.

3. The process as defined in claim 2, wherein said compounds are acetates.

4. The process as defined in claim 1, wherein said temperature is from 50° C. to 80° C.

5. The process as defined in claim 1, wherein each compound is present in an amount of from 0.05 to 0.5 weight % based on the acetaldehyde.

6. The process as defined in claim 1, wherein the product mixture, that is crude acetic acid and the catalytic mixture contained therein, is distilled to obtain a distillate containing acetic acid and the catalytic mixture-containing residue is recycled to the oxidation zone.

7. In a process for the preparation of acetic acid substantially free of formic acid by oxidation of acetaldehyde with oxygen in the liquid phase in the presence of a catalyst at a temperature of from 40° C. to 120° C., the improvement which comprises oxidizing liquid acetaldehyde in the presence of a catalytic mixture of cobalt, nickel and manganese compounds, one of said compounds being present in an amount up to five times the sum of the amounts of the other compounds; separating crude acetic acid containing catalytic mixture; distilling said crude acetic acid to obtain a distillate of low-boiling substances and acetic acid; distilling the distillate of said second distillation and further distilling the distillate of the third distillation; and returning to the oxidation zone the bottom product of said fourth distillation.

* * * * *